Figure 1:
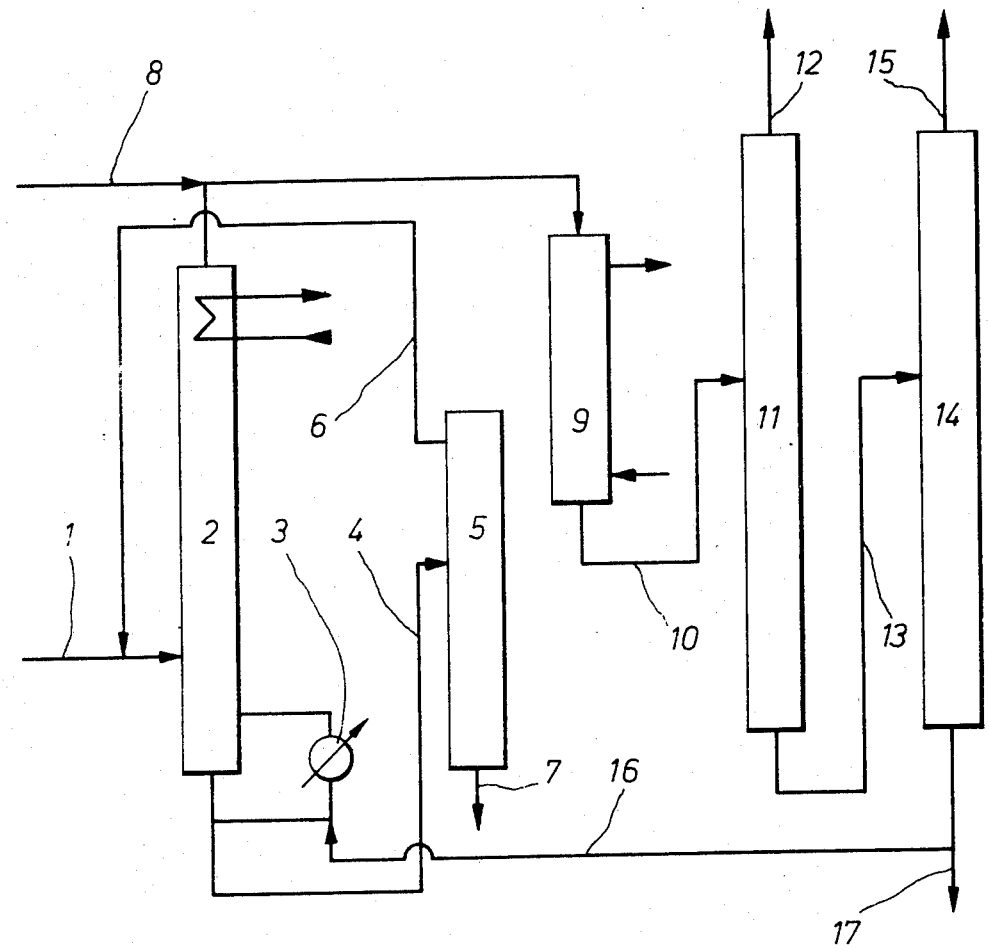

United States Patent [19]

Lauer et al.

[11] 4,048,242
[45] Sept. 13, 1977

[54] PROCESS FOR THE PRODUCTION OF CYCLOPENTENE FROM DICYCLOPENTADIENE

[75] Inventors: Hubert Lauer, Straberg; Norbert Schenk; Wulf Schwerdtel, both of Leverkusen, all of Germany

[73] Assignee: Bayer Aktiengesellschaft, Leverkusen, Germany

[21] Appl. No.: 575,661

[22] Filed: May 8, 1975

[30] Foreign Application Priority Data

May 24, 1974 Germany .............................. 2425289

[51] Int. Cl.$^2$ ............................ C07C 5/06; C07C 5/16
[52] U.S. Cl. ........................... 260/666 A; 260/666 DQ
[58] Field of Search ........................ 260/666 A, 666 D

[56] References Cited

U.S. PATENT DOCUMENTS

| | | | |
|---|---|---|---|
| 2,887,517 | 5/1959 | Noeske et al. | 260/666 D |
| 3,565,963 | 2/1971 | Tabler et al. | 260/666 D |
| 3,598,877 | 8/1971 | Fountain et al. | 260/666 D |
| 3,763,254 | 10/1973 | Engelhard et al. | 260/666 D |

FOREIGN PATENT DOCUMENTS 2,025,411   12/1971   Germany ........................ 260/666 D Primary Examiner—Veronica O'Keefe
Attorney, Agent, or Firm—Burgess, Dinklage & Sprung

[57] ABSTRACT

Producton of cyclopentene by splitting of dicyclopentadiene to produce cyclopentadiene and hydrogenating the cyclopentadiene to produce the cyclopentene in crude form, and distilling the crude cyclopentene to separate low boilers and high boilers therefrom and provide the cyclopentene product. The high boilers are recycled to the dicyclopentadiene splitting stage and serve to reduce resin formation in that stage. The process is particularly effective where the dicyclopentadiene has a low content of the so-called "codimers" which, if present in sufficient amount, would reduce resin formation.

17 Claims, 1 Drawing Figure

PROCESS FOR THE PRODUCTION OF CYCLOPENTENE FROM DICYCLOPENTADIENE

BACKGROUND

This invention relates to an economical process for the production of polymerisable cyclopentene by splitting dicyclpentadiene under the effect of heat to form cyclopentadiene, partially hydrogenating the cyclopentadiene formed to form crude cyclopentene and subsequently purifying the crude cyclopentene by distillation.

Cyclopentene is a monomeric hydrocarbon which is becoming increasingly more valuable for the production of polymers, for example for the production of high quality synthetic rubber (Hydrocarbon Processing, December, 1972, pages 72 to 75).

A preferred starting material for the production of cyclopentene by way of the intermediate stage cyclopentadiene is dicyclopentadiene. The dicyclopentadiene is preferably used in the form in which it accumulates as a reaction product in petrochemical hydrocarbon pyrolysis processes. In these pyrolysis processes, the dicyclopentadiene initially accumulates in the monomeric form as cyclopentadiene. For example, the $C_5$-fractions of naphtha crackers contain approximately 20% by weight of cyclopentadiene. Since a considerable outlay is involved in separating off the monomeric cyclopentadiene from such fractions and since the cyclopentadiene is not stable in storage on account of its ready conversion into the dimeric form, it is converted into the dimeric form by heat treatment and subsequently isolated by distillation from suitable fractions in the form of dicyclopentadiene. Accordingly, dicyclopentadiene may be regarded as the storage and transport form for cyclopentadiene. In this form, it also constitutes for example the starting material for the production of cyclopentene.

The cyclopentadiene is subsequently recovered from the storable and transportable dimeric form by splitting under heat. Accordingly, splitting of the dicyclopentadiene into cyclopentadiene forms the first stage of the process according to the invention. There are already a number of processes for splitting dicyclopentadiene into cyclopentadiene either in the gas phase or in the liquid phase. Since all these processes are carried out at elevated temperature, one of the more significant secondary reactions accompanying splitting is resinification of the dicyclopentadiene which can actually result in coking of the reaction vessels. Accordingly, processes for splitting dicyclopentadiene under heat into cyclopentadiene always includes measures for reducing or preventing resinification or coking in order to improve the yield of the splitting reaction.

In the gas-phase splitting of dicyclopentadiene, the consumption of energy and the danger of coking of the reaction tubes are particularly serious on account of the high reaction temperatures of around 400° to 500° C. In order to prevent coking, some processes are carried out with considerable quantities of inert diluting gases, such as steam, nitrogen, hydrogen and gaseous hydrocarbons (DOS No. 2,127,625). It is also known that a high rate of flow and minimal residence times may be maintained with a view to obtaining high yields (DOS No. 2,102,262).

The liquid-phase splitting of dicyclopentadiene is carried out at temperatures in the range of from about 160° to 240° C. Accordingly, far less outlay is involved.

On the other hand, splitting in the liquid phase involves longer residence times, for example of a few hours, which necessitate special precautions for reducing or completely preventing resinification of the apparatus used. Accordingly, the liquid-phase splitting of the dicyclopentadiene is generally carried out in the presence of high-boiling, inert diluents which are stable under the splitting conditions, in order to keep the resin products formed in solution. Thus, according to DAS No. 1,032,250 and U.S. Pat. No. 2,887,517, higher paraffin hydrocarbons are used as diluents. It is also known that splitting can be carried out with very low concentrations of cyclopentadiene (U.S. Pat. Nos. 2,387,993; 2,636,054 and 3,016,410).

One proven process for the liquid-phase splitting of dicyclopentadiene is described in DOS No. 2,019,596, the so-called codimers present in some streams of dicyclopentadiene (codimers are mixed dimers of cyclopentadiene, isoprene and piperylene which are very stable during splitting) being used as solvents for the resins formed. The advantage of this process is that the solvent used for the resins formed is already present in the system.

Accordingly, it can be said, in regard to the splitting of dicylopentadiene under heat to form cyclopentadiene as the first stage in the production of cyclopentene, that the most significant problem affecting this stage lies in the formation of secondary products as resins which can result in coking of the reaction vessels, and that, in addition to the actual splitting reaction, a number of measures have been proposed specifically with a view to eliminating resin formation.

The subsequent process stages of partial hydrogenation of the cyclopentadiene into cyclopentene and the further purification of the cyclopentene to the degree of purity required for polymerisation, present fewer difficulties by comparison with splitting. The yield of the dicyclopentadiene splitting stage also makes a greater contribution to the overall yield of the process for the production of cyclopentene than the following stages of partial hydrogenation and purification.

A complete process for the production of polymerisable cyclopentene is described in Hydrocarbon Processing, December '1972, pages 71 to 75. In that process, dicyclopentadiene is split in the liquid phase. The cyclopentadiene obtained is selectively hydrogenated, after which the crude cyclopentene obtained is purified in a fine fractionation stage. Dicyclopentadiene input streams with higher contents of so-called codimers (mixed dimers of cyclopentadiene, isoprene and piperylene) which, in liquid-phase splitting, serve as solvents for the resins formed, are used for the splitting reaction. To an increasing extent, however, the dicycloptenadiene fractions which have become commercially available in the meantime no longer have the high codimer content required for carrying out this process.

THE INVENTION

It has now suprisingly been found that polymerisable cyclopentene can be obtained in high yields from dicyclopentadiene by splitting the dicyclopentadine under heat to form cyclopentadiene, selectively hydrogenating the cyclopentadiene to form cyclopentene and purifying the cyclopentene by distillation, providing the fractions boiling at higher temperatures than cyclopentene which accumulate during purification by distillation are completely or partly recycled to the dicycylopentadiene splitting stage.

In one particularly advantageous embodiment of the process according to the invention, the fractions boiling at higher temperatures than cyclopentadiene are recycled in liquid form to the dicyclopentadiene splitting stage.

The process according to the invention will now be described in more detail.

There are various processes for splitting dicyclopentadiene, for example gas-phase splitting in a tubular furnace, for example, by the process described in DOS No. 2,127,625. Splitting of the dicycloptenadiene is preferably carried out in the liquid phase. For example, the dicyclopentadiene is split at temperatures in the range of from 160° to 240° C and preferably at temperatures in the range of from 180° to 200° C. The residence time is generally in the range of from 2 to 6 hours. Particularly good results are obtained with residence times of the dicyclopentadiene of from 3 to 5 hours. The apparatus normally used for splitting reactions may be used as the reaction vessel for the splitting stage. A so-called splitting column is preferably used. The energy required for splitting may be supplied through a sump-type circulation evaporator. The circulation may either be natural circulation or forced circulation. The sump of the evaporator may be surmounted by a separation column in which cyclopentadiene is separated from the unreacted dicyclopentadiene. A rectifying column of this kind may have approximately 10 practical plates. The rectifying column is best equipped with a dephlegmator in which a liquid reflux is obtained by partial condensation. The uncondensed cyclopentadiene fraction passes to the selective hydrogenation stage following addition of the hydrogen required for hydrogenation. High-boiling resin components formed in the splitting column are discharged from the sump of the splitting column. The non-reacted dicyclopentadiene and the codimers still contained in this product are separated off by rectification and recycled to the splitting column. A thin-layer evaporator is preferably used for the purpose of rectification. The cyclopentadiene may be hydrogenated by any of the usual processes in the liquid phase, in the gas phase or in mixed phase. Conventional hydrogenation catalysts may be used as catalysts. For example noble metal catalysts may be used, although base metal catalysts are also suitable. Hydrogenation of the cyclopentadiene is preferably carried out in the gas phase. Supported palladium catalysts are preferably used as the hydrogenation catalysts. Particularly suitable supporting materials for the palladium catalysts are lithium/aluminium spinel supports. It is particularly preferred to use a chromium- and titanium-modified palladium catalyst on lithium/aluminium spinel as support (DOS No. 2,025,411). Hydrogenation may be carried out under normal pressure or elevated pressure. The reaction vessel used for hydrogenation may, for example, be a tube reactor, in which case the heat of reaction is dissipated through a coolant circuit, for example filled with water, on the jacket side.

In addition to cyclopentene, the hydrogenation product generally contains small quantities of unreacted cyclopentadiene and cyclopentane as super-hydrogenation product, and also fractions of other $C_5$- and $C_6$-hydrocarbons which either were already present in the dicyclopentadiene stream used or are formed by splitting part of the codimers, if any, present in the dicyclopentadiene. In general, the starting material used for the process according to the invention is dicyclopentadiene with a codimer content of less than 7% by weight, preferably less than 5% by weight. Dicyclopentadiene with a content of less than 3% by weight is preferably used. Codimer contents in the starting dicyclopentadiene of less than 2% by weight are particularly preferred. It is also possible to use dicylopentadiene free from codimers. Dicyclopentadiene with higher codimer contents than those mentioned above may also be used.

The crude cyclopentene obtained by hydrogenation may be purified by the usual purification techniques. In general, it is purified by extractive distillation using selective solvents or by separation techniques based solely on distillation. Purification of the cyclopentene by distillation is preferably carried out by running off overhead in a first fractionating column a fraction boiling at lower temperatures than cyclopentene, consisting essentially of unreacted cyclopentadiene and acyclic $C_5$-hydrocarbons and distilling the sump product from the first fractionating column in a second fractionating column, the fractions boiling at higher temperatures than cyclopentene being run off from the sump as the so-called cyclopentane fraction, whilst pure cyclopentene distils off overhead.

The fraction boiling at a higher temperature than cyclopentene consists predominantly, e.g. in major proportion, or 30 to 95 wt.%, preferably 60 to 90 wt.% of cyclopentane. Depending upon the composition of the stream of dicyclopentadiene used, $C_6$-hydrocarbons, olefinic, paraffinic and/or aromatic compounds may also be present in this fraction, for example up to a content of 30% by weight. This fraction may also contain small quantities of dicyclopentadiene formed by re-dimersation from the non-hydrogenated cyclopentadiene fraction. Small quantities of cyclopentene, which have not been completely separated off in the fractionating column, may also be present.

By virtue of the process according to the invention, it is possible to obtain a significant improvement in the yield of the complete process by recycling to the splitting stage all or some of the fractions boiling at higher temperatures than cyclopentene which are obtained as the so-called cyclopentane fraction during purification of the crude cyclopentene by distillation in known manner. It is particularly advantageous to introduce this fraction in liquid form, for example immediately before the sump-type circulation evaporator, into the liquid-phase splitting reaction. The quantity of recycled product amounts to between 0.5 and ten times the quantity by weight of the dicyclopentadiene introduced. In one particularly economic procedure, the recycled cyclopentane fraction is 1 to 3 times the quantity by weight of the dicyclopentadiene used. In all cases, the yield of the complete process is significantly improved by comparison with processes in which no provision is made for recycling.

It must be regarded as extremely surprising that recycling those fractions of the overall process which boil at higher temperatures than cyclopentene to the dicyclopentadiene splitting stage in accordance with the invention, is highly effective in reducing resin formation and hence improves the over all yield of the process. It had by no means been expected that the presence of constituents of the so-called cyclopentene fraction from the purification of cyclopentene would favourably affect the formation of secondary products during the splitting of dicyclopentadiene, enabling the over all yield of the process to be improved.

The process according to the invention is illustrated in detail in FIG. 1 of the accompanying drawing and by the following Examples.

EXAMPLE 1

1107.8 g/h of dicyclopentadiene with the following composition:

| | |
|---|---|
| $C_5$-hydrocarbons | 0.45% by weight |
| dicyclopentadiene | 97.94% by weight |
| codimers | 1.03% by weight |
| tricyclopentadiene | 0.58% by weight |
| | 100.0% by weight | were continuously pumped through (1) of FIG. 1 into the sump of a splitting column (2), in which the dicyclopentadiene was split in liquid phase at a temperature of 180° C over a residence time of about 3 hours. The heat required for the splitting reaction was delivered by a steam-heated sump-type natural-circulation evaporator (3). In a 1 meter long packed fractionating column fitted to the sump, the split dicyclopentadiene was separated off from unreacted dicyclopentadiene. The fractionating column was equipped with a water-cooled dephlegmator in which some of the split cyclopentadiene was condensed and recycled to the splitting column.

448 g/h were continuously removed from the sump of the splitting column through (4) and rectified in a thin-layer evaporator (5). 273 g/h of head product were returned to the splitting column through (6). 175 g/h of sump product, which had a resin content of 94,7 % by weight were completely discharged from the process through (7). The thin-layer evaporator had an evaporator surface of 400 sq. cm. and was heated with a heating circulation to 200°C.

Following the addition of 480 1/h of 80% hydrogen through (8), the cyclopentadiene gas issuing from the splitting column was selectively hydrogenated on 600 ml of a palladium-chromium catalyst to form cyclopentene. The catalyst was fixedly arranged in a vertical, 1500 mm long and 25 mm diameter tube (9) heated with warm water. The gas mixture to be hydrogenated was passed downwards over the catalyst. The warm water heating the tube was adjusted to a temperature of 60° C.

The hydrogenated product, including the excess hydrogen and the inert gases, were introduced through (10) into a first fractionating column (11) in which 7.8 g/h of a fraction boiling at a lower temperature than cyclopentene, together with hydrogen and inert gases, were removed overhead through (12). The column had a diameter of 76 mm and was packed to a height of 10 meters. The sump product of this column was introduced through (13) into a second fractionating column (14) with the same dimensions, in which a fraction boiling at a higher temperature than cyclopentene was removed via the sump, whilst the pure cyclopentene was removed overhead through (15).

| The sump fraction contained: | |
|---|---|
| cyclopentane | 88.8% by weight |
| cyclopentene | 9.6% by weight |
| higher hydrocarbons | 1.6% by weight |
| | 100.0% by weight |

1000 g/h of this fraction were recycled through (16) in liquid form to the splitting column before the sump-type circulator evaporator. 10 g/h of the sump fraction were removed from the process circuit through (17).

1000 g/h of this fraction were recycled in liquid form to the splitting column before the sump-type circulation evaporator. 10 g/h of the sump fraction were removed from the process circuit.

933.6 g of pure cyclopentene with the following composition were obtained:

| | |
|---|---|
| cyclopentene | 96.11% by weight |
| cyclopentane | 3.89% by weight |

Accordingly, the yield of cyclopentene amounts to: quantity of cyclopentene × cyclopentene content × 100

$$\frac{933.6 \times 96.11}{1107.8 \times 97.94} = 82.7\%$$

This Example shows that cyclopentene can be obtained in excellent yields from streams of dicyclopentadiene substantially free from codimer by the process according to the invention.

EXAMPLE 2 (Comparison Example)

996.3 g/h of dicyclopentadiene with the same composition as in Example 1 were introduced into the apparatus described in Example 1 and FIG. 1, and Example 1 was repeated except as noted herein.

However, the sump product of the second fractionating column was not recycled through (16) of the splitting stage. Otherwise the procedure was as described in Example 1. The quantity of hydrogen required for hydrogenation amounted to 386.5 1/h (80%).

The quantities accumulating were as follows:

| | | |
|---|---|---|
| sump product from the thin-layer evaporator | 256.4 | g/h |
| low-boiling fraction | 45.95 | g/h |
| high-boiling fraction | 94.84 | g/h |
| pure cyclopentene | 624.52 | g/h | composition of the pure cyclopentene:

| | |
|---|---|
| cyclopentene | 98.91% by weight |
| cyclopentane | 1.09% by weight |

Calculated in the same way as in Example 1, the yield of cyclopentene amounted to:

$$\frac{624.52 \times 98.91 \times 100}{996.3 \times 97.94} = 63.3\%$$

It is clear that, without the recycling according to the invention, the yield of cyclopentene is much lower.

EXAMPLE 3

1211.1 g/h of a dicyclopentadiene with a relatively high codimer content were introduced into the apparatus described in Example 1 and FIG. 1. The composition of the dicyclopentadiene was as follows:

| | |
|---|---|
| $C_5$-hydrocarbons | 0.9% by weight |
| dicyclopentadiene | 90.18% by weight |
| codimers | 7.06% by weight |
| tricyclopentadiene | 1.86% by weight |
| | 100.00% by weight |

The quantity of hydrogen required for hydrogenation amounted to 467 l/h (80%). The recycling of the fraction boiling at a higher temperature than cyclopentene to the splitting stage before the evaporator amounted to 1000 g/h. This stream had the following composition:

| | |
|---|---|
| cyclopentane | 60.44% by weight |
| cyclopentene | 10.83% by weight |
| n-hexane | 1.8% by weight |
| benzene | 9.54% by weight |
| methyl cyclopentane | 13.07% by weight |
| methyl cyclopentene | 2.55% by weight |
| other C$_6$-hydrocarbons | 0.71% by weight |

The quantities removed from the process were as follows:

| | | |
|---|---|---|
| sump product from thin-layer evaporator | 250.0 | g/h |
| low-boiling fraction | 26.75 | g/h |
| high-boiling fraction | 43.91 | g/h |
| cyclopentene | 904.9 | g/h |

The composition of the pure cyclopentene was as follows:

| | |
|---|---|
| cyclopentene | 99.13% by weight |
| cyclopentane | 0.84% by weight |
| C$_6$-hydrocarbons | 0.03% by weight |

Calculated in the same way as in Example 1, the yield of cyclopentene amounted to:

$$\frac{904.9 \times 99.13 \times 100}{1211.1 \times 90.18} = 82.13\%$$

What we claim is:

1. In a process for the production of cyclopentene from dicyclopentadiene which comprises splitting dicyclopentadiene under heat to form cyclopentadiene; partially hydrogenating the cyclopentadiene to form a crude cyclopentene containing an impurities fraction boiling at a higher boiling point than cyclopentene and containing cyclopentane; purifying the crude cyclopentene by distillation in which said impurities fraction is separated from the crude cyclopentene; the improvement which comprises recycling at least part of the separated impurities fraction as the impurities fraction is produced in said distillation to the dicyclopentadiene splitting stage, said separated impurities fraction comprising predominantly cyclopentane.

2. A process as claimed in claim 1, wherein the recycled impurities are recycled in liquid form.

3. A process as claimed in claim 1, wherein the weight of the recycled impurities is from 0.5 and 10 times the weight of the dicyclopentadiene introduced into the process.

4. A process as claimed in claim 1, wherein the dicyclopentadiene is split in the liquid phase in a splitting column in which the residence time is 2 to 6 hours and the temperature is in the range of from 160° to 240° C.

5. A process as claimed in claim 2, wherein the dicyclopentadiene is split in the liquid phase in a splitting column in which the residence time is 2 to 6 hours and the temperature is in the range of from 160° to 240° C.

6. A process as claimed in claim 1, wherein the cyclopentadiene is hydrogenated in the gas phase in the presence of a palladium catalyst on lithium-aluminium spinel.

7. A process as claimed in claim 1, wherein during the purification of the cyclopentene by distillation, a fraction boiling at a lower temperature than cyclopentene is obtained as head product in a first fractionating column; the sump product of the first fractionating column is distilled in a second fractionating column from which a fraction boiling at a higher temperature than cyclopentene is removed as said impurities fraction.

8. A process as claimed in claim 2, wherein during the purification of the cyclopentene by distillation, a fraction boiling at a lower temperature than cyclopentene is obtained as head product in a first fractionating column; the sump product of the first fractionation column is distilled in a second fractionating column from which a fraction boiling at a higher temperature than cyclopentene is removed as said impurities fraction.

9. A process as claimed in claim 1, wherein the dicyclopentadiene introduced into the process contains up to about 7% by weight of codimer.

10. A process as claimed in claim 1, wherein the dicyclopentadiene introduced into the process contains up to about 5% by weight of codimer.

11. A process as claimed in claim 1, wherein the dicyclopentadiene introduced into the process contains up to about 3% by weight of codimer.

12. A process as claimed in claim 1, wherein the dicyclopentadiene introduced into the process contains up to about 2% by weight of codimer.

13. A process as claimed in claim 1, wherein the dicyclopentadiene is split in the liquid phase.

14. A process as claimed in claim 2, wherein the dicyclopentadiene is split in the liquid phase.

15. A process as claimed in claim 1, wherein said impurities fraction comprises 30 to 95 wt.% of cyclopentane.

16. A process as claimed in claim 1, wherein said impurities fraction comprises 60 to 90 wt.% of cyclopentane.

17. A process as claimed in claim 16, wherein the dicyclopentadiene is split in liquid phase.

* * * * *